United States Patent
Siess

(10) Patent No.: US 12,399,109 B2
(45) Date of Patent: Aug. 26, 2025

(54) OPTICAL PROPERTY MEASUREMENT USING A SENSOR BEHIND A DISPLAY SCREEN

(71) Applicant: ams Sensors Germany GmbH, Jena (DE)

(72) Inventor: Gunter Siess, Kraftsdorf (DE)

(73) Assignee: ams Sensors Germany GmbH, Jena (DE)

( * ) Notice: Subject to any disclaimer, the term of this patent is extended or adjusted under 35 U.S.C. 154(b) by 0 days.

(21) Appl. No.: 17/771,797

(22) PCT Filed: Oct. 29, 2020

(86) PCT No.: PCT/EP2020/080402
§ 371 (c)(1),
(2) Date: Apr. 25, 2022

(87) PCT Pub. No.: WO2021/094097
PCT Pub. Date: May 20, 2021

(65) Prior Publication Data
US 2022/0364983 A1   Nov. 17, 2022

Related U.S. Application Data

(60) Provisional application No. 62/936,898, filed on Nov. 18, 2019, provisional application No. 62/934,779, filed on Nov. 13, 2019.

(30) Foreign Application Priority Data

Jun. 18, 2020 (GB) .................................. 2009352

(51) Int. Cl.
*G01N 21/25* (2006.01)
*G01N 21/27* (2006.01)
*G01N 33/483* (2006.01)

(52) U.S. Cl.
CPC ......... *G01N 21/251* (2013.01); *G01N 21/255* (2013.01); *G01N 21/274* (2013.01);
(Continued)

(58) Field of Classification Search
CPC .. G01N 21/251; G01N 21/255; G01N 21/274; G01N 33/4833; G01N 2201/0628; G01N 2201/127
See application file for complete search history.

(56) References Cited

U.S. PATENT DOCUMENTS 9,671,329 B2 * 6/2017 Hennebelle ........... G01J 3/0272
10,216,975 B1 * 2/2019 He ....................... G06V 10/143
(Continued)

FOREIGN PATENT DOCUMENTS

CN   109154961 A   1/2019
CN   109196525 A   1/2019
(Continued)

OTHER PUBLICATIONS

C. H. Brown Elliott, T. L. Credelle, S. Han, M. H. Im, M. F. Higgins, P. Higgins; Development of the PenTile Matrix™ color AMLCD subpixel architecture and rendering algorithms; Jun. 18, 2012; pp. 89-98 (Year: 2012).*

(Continued)

*Primary Examiner* — Tarifur R Chowdhury
*Assistant Examiner* — Kemaya Nguyen
(74) *Attorney, Agent, or Firm* — Michael Best & Friedrich LLP

(57) ABSTRACT

Optical property measurement using a sensor behind a display screen Examples of this application disclose a method for measuring optical properties of a target. The method comprises illuminating the target with an illumination area with a display screen in contact with the target, and analysing signals reflected from the target and transmitted (Continued)

back through the display screen to a sensor positioned behind the display screen, to determine the optical properties of the target.

18 Claims, 3 Drawing Sheets

(52) U.S. Cl.
CPC .. *G01N 33/4833* (2013.01); *G01N 2201/0628* (2013.01); *G01N 2201/127* (2013.01)

(56) References Cited

U.S. PATENT DOCUMENTS

| | | | |
|---|---|---|---|
| 10,282,582 B2* | 5/2019 | Setlak | G06V 40/1318 |
| 2002/0005954 A1 | 1/2002 | Sperling | |
| 2006/0255275 A1* | 11/2006 | Garman | G01J 5/084 |
| | | | 250/338.1 |
| 2011/0090048 A1 | 4/2011 | Li et al. | |
| 2014/0178060 A1* | 6/2014 | Saita | G02B 5/005 |
| | | | 396/505 |
| 2018/0143076 A1 | 5/2018 | Sheridan et al. | |
| 2019/0303639 A1 | 10/2019 | He et al. | |

FOREIGN PATENT DOCUMENTS

| | | |
|---|---|---|
| CN | 109923555 A | 6/2019 |
| EP | 3533388 A1 | 9/2019 |
| WO | WO-2020154926 A1 * | 8/2020 |

OTHER PUBLICATIONS

S. -H. Chae, C. -H. Yoo, J. -Y. Sun, M. -C. Kang and S. -J. Ko, "Subpixel rendering for the pentile display based on the human visual system," in IEEE Transactions on Consumer Electronics, vol. 63, No. 4, pp. 401-409, Nov. 2017 (Year: 2017).*
United Kingdom Search Report for corresponding GB Patent Application No. 2009352.2 dated Nov. 16, 2020.
International Search Report for corresponding International Application No. PCT/EP2020/080402, mailed Feb. 3, 2021.
Chinese Patent Office Action for Application No. 202080079145.9 dated Jan. 24, 2025 (14 pages including English machine translation).
Chinese Patent Office Action for Application No. 202080079145.9 dated Jul. 14, 2025 (8 pages including English translation).

* cited by examiner

OPTICAL PROPERTY MEASUREMENT USING A SENSOR BEHIND A DISPLAY SCREEN

TECHNICAL FIELD OF THE DISCLOSURE

The disclosure relates to an optical property measurement using a sensor behind a display screen particularly but not exclusively, to a method for measuring the color and grade of translucency of a target.

BACKGROUND OF THE DISCLOSURE

The present disclosure relates to a method for measuring optical properties of a target by using an illuminating display screen and a sensor positioned behind the display screen. In particular, but not exclusively, the method is used to determine the color and grade of translucency of a target.

When light reflects off an object, depending on the properties of the object, light is, in some combination, either reflected, scattered or absorbed. The interpretation of color is the human interpretation of the combination of scattered and reflected light from an object, which in itself, consists of a specific distribution of wavelengths or spectra in the visible spectrum (VIS).

In order to measure the true color of an object, all the reflected (specular component) and scattered light (diffuse component) off an object must be captured. The perceived color of an object cannot be absolutely measured, but can be measured relative to another perceived color. In this approach, the specular component is excluded so that the diffuse component is the dominant signal. This diffuse component concerns the surface conditions of the object and provides information as to the gloss, finish and texture. To measure the relative perceived color of an object, a standard measurement geometry is adopted to remove specular reflections.

An example configuration known to the prior art consists of a (0°/45° or 45°/0°) setup. In this setup, the illumination source is positioned at 45° to the surface normal (0°) and the sensor is positioned along the surface normal. However, for diffuse reflecting targets, which generate a larger fraction of reflected diffuse light than specular light, this geometry restriction is less stringent.

In the color measurement of translucent objects, light penetrates the object, but is also scattered by the object. The scattered light may scatter multiple times before exiting the object at an angle different to that of entry. The amount of scattering of light depends on the wavelength of the light. In some objects, longer wavelength regions of the incident light are scattered more in the object. In other objects, smaller wavelength regions of the incident light are scattered more in the object.

Currently, in the prior art, under near-field setup conditions, there is a problem in capturing all the reflected light for translucent objects. In this case, light from an illumination area on a translucent object will diffuse scatter and some wavelength regions will be either scattered too much or too little and will not return through the sensor aperture to be captured. Translucent object true color determination under these conditions is therefore difficult to measure accurately, as spectral information is inevitably lost. The process of scattering within a material is complex, and cannot be easily compensated.

To present, the known solutions to the prior art for avoiding the loss of spectral information in the true color measurement of translucent materials is to either: use a small illumination area on the target and a large measurement spot, or, use a large illumination area on the target and a small measurement spot. This is illustrated in FIGS. 1A. and 1B. respectively. In the first method, the measurement spot must be large enough to capture all the scattered light. This requires an enormous sensor and device. In the second method, the illumination area needs to be so large that the combination of many different scattering events acts to produce the complete spectra in the measurement spot. This is only true for a small measurement spot area and depends on the degree of scattering, or translucency, within the object.

It is therefore an aim of the present disclosure to provide a method that addresses one or more of the problems above or at least provides a useful alternative.

SUMMARY

In general, this disclosure proposes to overcome the above problems by using a display screen, with a non-zero transmission function in at least part of the visible spectrum, to illuminate the target. The non-zero transmission function allows the target to be placed in contact with the display, therefore producing the large illumination area but a small measurement spot criterion for reliable color measurement. Furthermore, it is possible to apply colored patterns to the target with a single illumination device, without a large separation between light source and the target, thus reducing the configuration size. This arrangement enables color measurement, a grade of translucency measurement and a reconstruction of the re-emission spectrum for the target.

According to a first aspect of the present invention, there is provided a method for measuring optical properties of a target. A display screen is provided. The target is illuminated with an illumination area on the display screen, while the target is in contact with the display screen. A sensor is provided, positioned behind the display screen to receive light reflected from the target and transmitted back through the display screen. The signals obtained from the sensor during illumination are analysed to determine the optical properties of the target.

Further embodiments are defined in claim 2 et seq.

In the prior art, particular configurations are required to measure the perceived color of an object. For example, the (0°/45° or 45°/0°) setup. However, these methods require a significant amount of space. In a near field set-up, translucent materials diffuse scatter light which results in a loss of spectral information, which is often dominated at one side of the optical range. The process of reflection in translucent materials is complex and therefore spectral information cannot be easily compensated. Therefore, color measurement of translucent materials requires either a small illumination spot and a large measurement spot, to ensure that spectral information is not scattered and lost, or, a large illumination spot and a small measurement spot. In the prior art, both these methods require significant space.

Compared to known systems, the present optical property measurement method using a sensor behind a display screen, has the following advantages. It reduces the size of the set-up area for optical property measurement and therefore simplifies the methods in the prior art. It also enables novel methods for illuminating the target with patterned and/or colored regions.

Finally, the present optical property measurement method using a sensor behind a display screen disclosed here utilises a novel approach at least in that the display screen is in contact with the target, and that the sensor is positioned behind the illuminating device and capable of measuring optical properties such as, the color of the target, the grade of translucency of the target and reconstruct the re-emission spectra of the target.

BRIEF DESCRIPTION OF THE DRAWINGS

Some examples of the disclosure will now be described by way of example only and with reference to the accompanying drawings, in which.

DETAILED DESCRIPTION

In order to provide improved colour measurement of target materials, in particular translucent materials, a procedure is proposed below in which the target material is illuminated with a display screen in contact with the target, and the reflected signals are detected by a sensor located behind the display screen, and analysed.

Figure 1A:
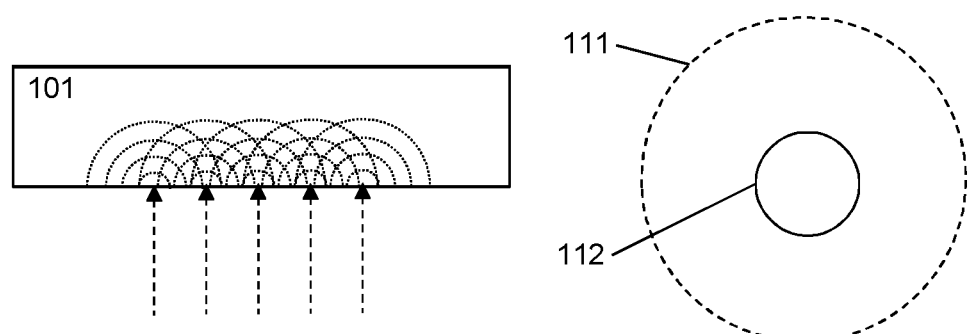
FIGS. 1A and 1B show a simplified schematic of the measurement set-ups compatible with determining color measurement of a translucent material.
Figure 1B:
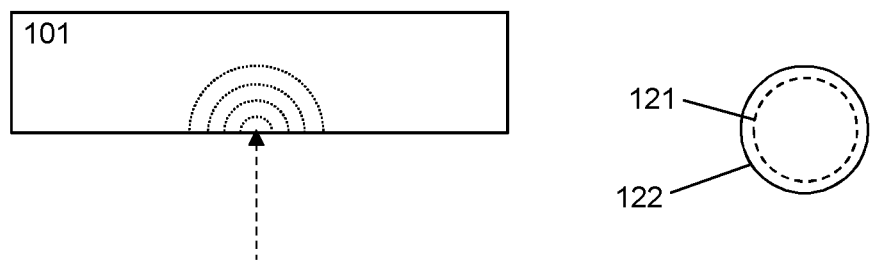

FIGS. 1A and 1B show the constraints on the illumination required to measure transparent materials. There, are, broadly, two possible approaches. The first approach, shown in FIG. 1A, is a broad illumination spot 111 on the target 101, with the measurement 112 taking place only at the centre of the spot (i.e. where the illumination is brightest). This is inefficient, as most of the reflected light is not measured, but it allows all parts of the reflection to be picked up (e.g. the sensor will receive the direct reflection for the central rays of the illumination, and the indirect reflection for the outer rays). The second approach, shown in FIG. 1B, is to use a narrow illumination spot 121, with the measurement 122 surrounding the illumination spot to capture all the reflected light. This is more energy efficient, since all the light is captured, but it requires a large sensor.

Figure 2:
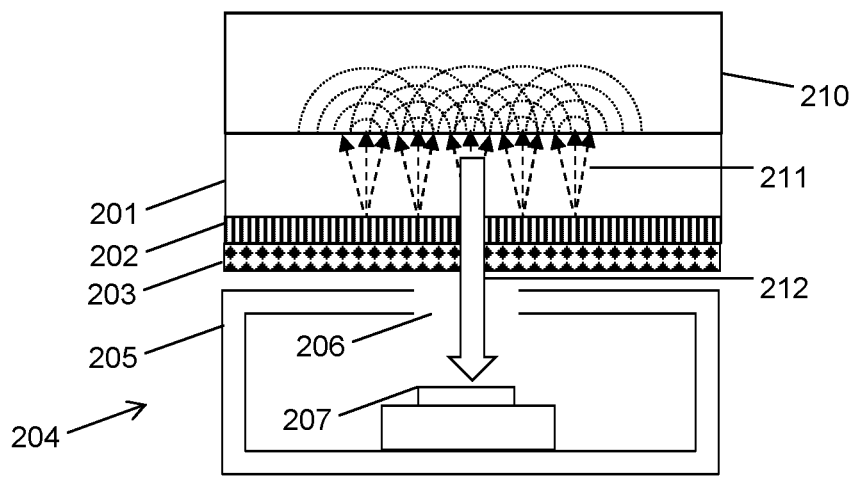
FIG. 2 shows a simplified schematic of the device for carrying out the method of measuring the optical properties of a target material, in accordance with the present disclosure.

FIG. 2 is a schematic illustration of a device according to the present disclosure. The device comprises a display screen 201, having a backing 202 and an optional diffuser or filter 203 located behind the backing. Behind the display screen, backing and diffuser or filter is located a sensor assembly 204, comprising a housing 205 having an aperture 206 (e.g. of 1 mm diameter), and a light sensor 207. To perform a measurement of a target material, the display screen 201 is placed in contact with the material 210, and provides illumination 211 to the material. The light 212 reflected from the material passes through the display screen and the aperture, and is detected by the light sensor 207. The signals received by the sensor during illumination can then be used to determine the optical properties of the target.

The illumination provided by the display screen is a coloured region (e.g. a primary colour, a secondary colour, or white). The reflected light can be used to determine how the target material scatters light, and therefore determine how transparent the material is.

The size, shape, and position of the illumination are provided by the display screen may be varied, and analysis carried out with each successive illumination pattern, and by comparing the results between illumination patterns. This can be useful, for example, to detect defects in the target material and determine their location (as these will reflect differently, but only when illuminated by the display screen). In general, the illumination area will be centred on an axis of the sensor, but this is not required.

Figure 3A:
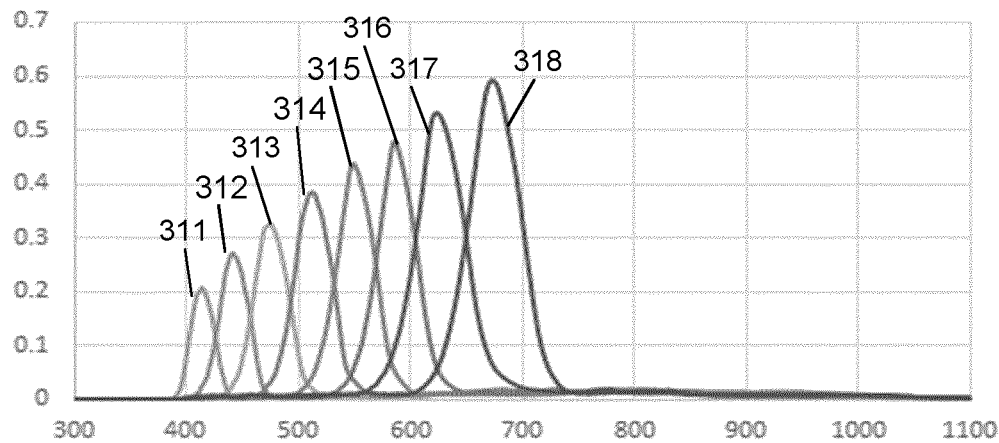
FIGS. 3A and 3B show the correction to the system sensitivity based on the transmission function of a OLED display screen, in accordance with the present disclosure.
Figure 4A:
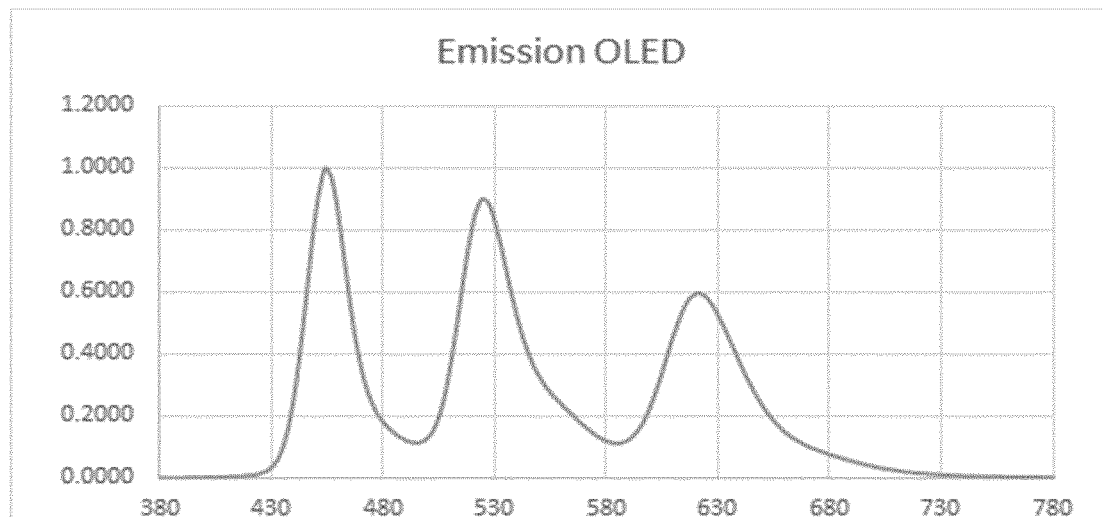
FIGS. 4A and 4B show an exemplary emission and transmission function respectively for an OLED display screen, in accordance with the present disclosure.

As is usual for optical sensors, the sensor output will need to be calibrated based on the sensor sensitivity. A graph of sensitivity for an example multi-spectral sensor is shown in FIG. 3A. As can be seen in the figure, the sensor has several transmission peaks 311, 312, 313, 314, 315, 316, 317 and 318, each of which corresponds to one of the sensor channels. Calibration will also be based on the light output—i.e. the emission function of the display screen (shown for an OLED in FIG. 4A), and the pattern displayed.

Figure 3B:
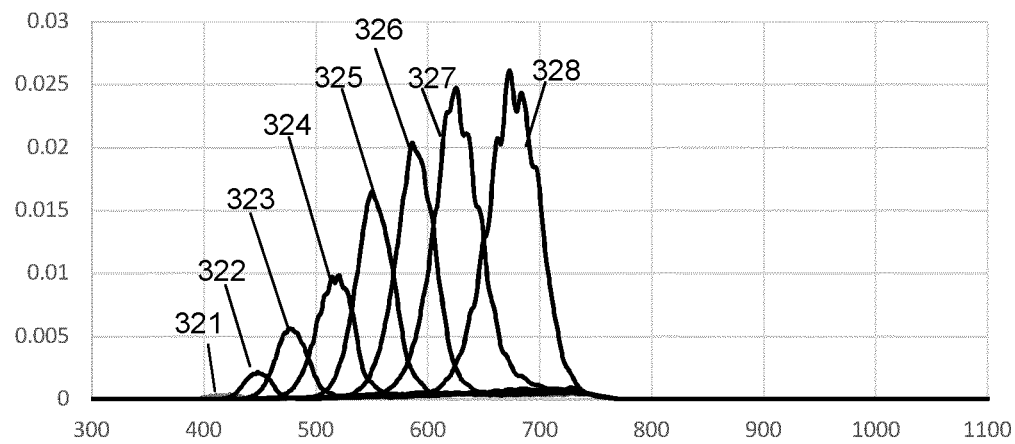
Figure 4B:
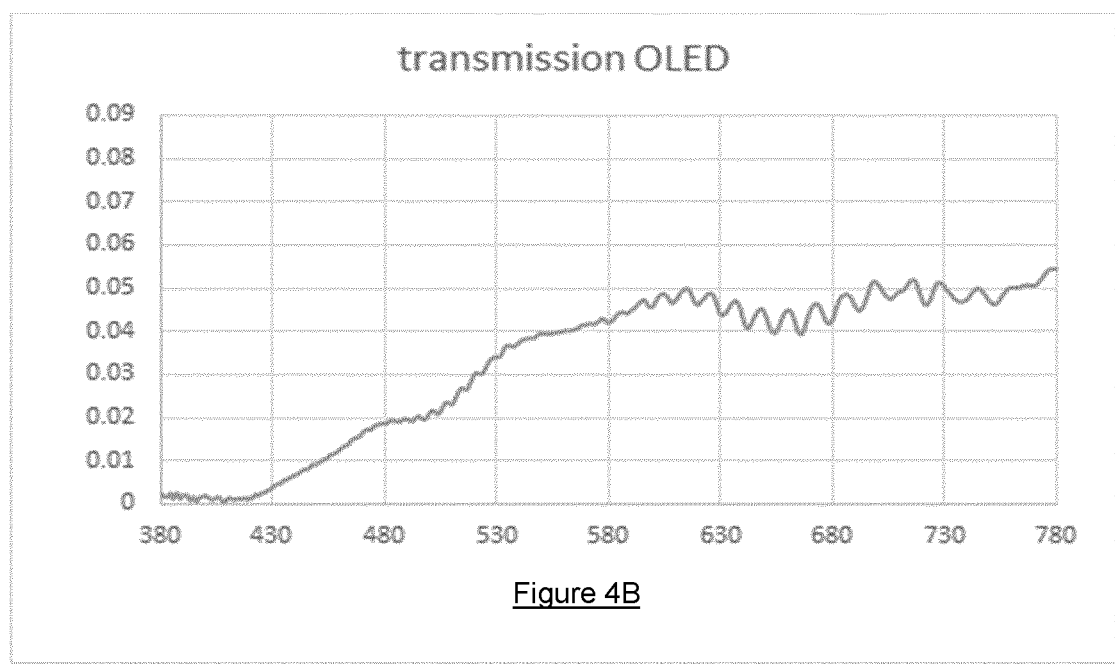

In the device described above, the calibration may be improved by also taking into account the transmission function of the display screen (and any other components in front of the sensor) which is shown in FIG. 4B for an OLED. FIG. 3B shows the adjusted sensitivity of the same sensor as in FIG. 3A, when placed behind a display screen with the transmission function shown in FIG. 4B. Each of the peaks 321, 322, 323, 324, 325, 326, 327, 328 corresponds to one of the peaks in FIG. 3A, but their height and shape has changed significantly (note the different scale on the two graphs) to account for the reduced transmission of light by the display screen.

To aid in calibration, the transmission function may be measured relative to a material of known reflectance—e.g. taking a material with known optical properties, measuring the material using the method described above, and then adjusting the calibration so that the output matches the known optical properties of the material. This calibration, or any other suitable recalibration, may be done periodically to account for changes in the transmission of the display screen or sensitivity of the sensor over time, or may be performed prior to each measurement of a target material with unknown properties.

Other techniques as known in the art, such as taking multiple measurements and averaging them, may be used to improve the accuracy of the measured results.

Obtaining a broad spectrum measurement of the optical properties of the material may be done with white light, or alternatively it may be done by sequentially illuminating the target material with different colours of light (e.g. from each pixel colour in the display) and concatenating all of the measured reflection functions (or, during calibration, all of the measured transmission functions of the display screen).

Whether the illumination comprises a coloured pattern or a white pattern, the remainder of the display screen will generally be black—though this is not strictly required.

The shape of the illumination on the display screen may be a circle, or another pattern with circular symmetry such as a ring, or a series of concentric rings of varying thickness and/or colour. In general, though, the pattern may be any image which is capable of being formed by the display screen, and the sensor can be calibrated accordingly.

Where the target material has some kind of pre-existing feature or division (e.g. a target consisting of two materials attached together at a join, or a target having a flaw in its material), the shape of the illumination may be varied to account for that feature or division (e.g. illuminating the material on each side of the join differently, or choosing a pattern in order to locate the flaw).

The sensor may be a three-channel sensor or a multi spectral sensor. Suitable multi spectral sensors include the AS7341 multi-spectral sensor (which has 8 channels), or other sensors having at least 4 channels.

The measured optical properties of the target may include a colour measurement, which may be converted into a colour space such as RGB or XYZ. The conversion into the colour space may be performed by a matrix operation, multiplying the output signal vector from the sensor by an [N×M] matrix, where N is the number of sensor channels, and M is the number of dimensions in the colour space. For example, conversion between a 3-channel sensor and the RGB colour space would require a 3×3 matrix, and conversion between an 8-channel sensor and the XYZ colour space would require an 8×3 matrix. The matrix may be determined by calibration of the sensor as described above.

The measured optical properties may also include a reconstructed emission spectrum, which may be similarly calculated using an [N×M] matrix, where M is the number of "bins" in the emission spectrum model.

The measured optical properties may include a grade of translucency, which may be determined by varying the size and/or shape of the illumination area to determine the change in scattered light. For example, the illumination shape may be a circle centred on the sensor, and the size may be varied. For small illumination sizes, all the scattered light is captured. For larger illumination sizes, less scattered light is captured—but the spectrum and proportion of the scattered light captured will depend on the translucency properties of the material. By analysing each measured signal for each different illumination size, and comparing them, and grade of translucency may be assigned to the target material. For example, this may be based on an increased contribution of a particular frequency region within the scattered light spectrum at certain sizes.

Other standard algorithms as known to those skilled in the art may be used to convert the measured reflections in each band of the sensor to colours, emission spectra, translucency measurements, or other optical properties.

The display screen may be an organic light emitting diode (OLED) screen, or any other suitable illumination source capable of emitting light and having a non-zero transmission function over at least part of the visible spectrum. Preferably, this would have a non-zero transmission function over the entire visible spectrum, but this is not required.

As previously mentioned, an additional optical device such as a filter or diffuser may be placed between the display screen and the sensor, either behind or in front of the aperture. A diffuser may be used to reduce the effect of scattering inhomogeneity in the target material, allowing determination of average optical properties. A filter may be used to block near-infra red, ultra violet, or other unwanted light.

The sensor behind the display screen may also be used as an ambient light sensor when a target material is not in place (and this would not require illumination).

As an example use case, the target material may be skin, and the method may be used by placing the display on a person's skin to obtain colour, translucency, and other optical information. This data may then be used, for example, for skin-tone matching in the cosmetic industry.

Examples of the present disclosure can be employed in many different applications, including color measurement in the textile and paint industry, skin-color matching in the cosmetic industry, defect detection measurement in mechanical industries and is particularly well-suited for optical property measurement in translucent materials as well as in other industries.

The invention is defined by the appended claims, and in particular is not limited by the examples disclosed above. "Comprising" should be taken to mean that the relevant object includes the listed features, but may also contain other features. Any references to the singular include the plural, where appropriate—and where actions are performed by a processor or other computing device, the functions of several processors may be combined into one processor, or vice versa. Features disclosed in separate examples, or in separate dependent claims, may be combined as appropriate, and any reference numerals appearing in the claims should not be taken as limiting their scope.

LIST OF REFERENCE NUMERALS

101 Target material for measurement
111 Illumination spot on the target
112 Measurement area
121 Illumination spot on the target
122 Measurement area
201 Display screen
202 Backing of display screen
203 Diffuser or filter (optional)
204 Sensor assembly
205 Housing
206 Aperture
207 Light sensor
210 Target material
211 Illumination
212 Reflected light
311 to 318 Sensitivity of channels in a multi-spectral sensor
321 to 328 Sensitivity of channels in a multi-spectral sensor corrected with the transmission function of the display screen

The invention claimed is:

1. A method for measuring optical properties of a target comprising:
providing a display screen;
illuminating the target with an illumination area on the display screen, wherein the target is in contact with the display screen;
providing a sensor positioned behind the display screen to receive light reflected from the target and transmitted back through the display screen;
determining a change in scattered light by varying a size or shape of the illumination area; and
determining a grade of translucency of the target based on the change in scattered light, wherein determining the grade of translucency is done by analysing signals from the sensor during illumination including comparing signals detected for a first varied illumination area to signals detected for a second varied illumination area.

2. The method according to claim 1, wherein the illumination area is centered on a sensor axis.

3. The method according to claim 1, wherein a signal is corrected for with a calibration function includes:
a sensitivity of the sensor; and
a transmission function of the display screen, wherein the transmission function is non-zero in at least a part of in a visible spectrum.

4. The method according to claim 1, wherein the illumination area includes a white pattern and a remaining portion of the display screen is black.

5. The method according to claim 1, wherein the illumination area includes a colored pattern and a remaining portion of the display screen is black.

6. The method according to claim 5, wherein the illumination area includes emission from each pixel color in the display sequentially.

7. The method according to claim 1, wherein a shape of the illumination area on the display screen is substantially a circle.

8. The method according to claim 1, wherein the sensor includes one of:
   a three channel color sensor;
   a multi-spectral sensor.

9. The method according to claim 8, wherein the multi-spectral sensor includes eight channels.

10. The method according to claim 1, wherein the optical properties include a color measurement.

11. The method according to claim 10, wherein the color measurement is converted into a color space.

12. The method according to claim 11, wherein the color space is one of:
    RGB; and
    XYZ.

13. The method according to claim 1, wherein the optical properties include a reconstructed re-emission spectrum.

14. The method according to claim 1, wherein the optical properties include a grade of translucency.

15. The method according to claim 1, wherein the display screen includes an organic light-emitting diode, OLED, display screen.

16. The method according to claim 1, wherein an additional optical device is placed in between the display screen and the sensor, wherein the additional optical device includes one or both of a diffuser and a filter.

17. The method according to claim 16, wherein the filter is blocking in a near-infrared, NIR, range.

18. The method according to claim 1, wherein the target includes skin.

* * * * *